United States Patent

Berger et al.

Patent Number: 5,491,148
Date of Patent: Feb. 13, 1996

[54] ISOQUINOLINONE AND DIHYDROISOQUINOLINONE 5-$HT_3$ RECEPTOR ANTAGONISTS

[75] Inventors: Jacob Berger, Los Altos Hills; Robin D. Clark, Palo Alto, both of Calif.

[73] Assignee: Syntex (U.S.A.) Inc., Palo Alto, Calif.

[21] Appl. No.: 692,407

[22] Filed: Apr. 26, 1991

[51] Int. Cl.[6] .................. A61K 31/44; C07D 453/02
[52] U.S. Cl. .................. 514/305; 514/307; 546/126; 546/133; 546/137; 546/141; 546/142
[58] Field of Search .................. 546/133, 137, 546/126, 141, 142; 514/305, 307

[56] References Cited

U.S. PATENT DOCUMENTS 4,959,367  9/1990  King.

FOREIGN PATENT DOCUMENTS 0093488  9/1983  European Pat. Off..
0430190  11/1990  European Pat. Off..

OTHER PUBLICATIONS

Reynolds, J. C., *Prokinetic Agents: A Key in the Future of Gastroenterology*, Gastroenterology Clinics of North America, vol. 18, No. 2, Jun. 1989, pp. 437–457 (Reynolds).
*Drugs Acting on 5–Hydroxytryptamine Receptors*, The Lancet, Sep. 23, 1989, pp. 717–719.
Peatfield, R., *Drugs and the Treatment of Migraine*, Trends. Pharmacol. Sci., 1988, vol. 9, pp. 141–145.
Scholtysik, et al., *5–Hydroxytryptamine Antagonist ICS 205–930 Blocks Cardiac Potassium, Sodium and Calcium Currents*[1], J. Pharmacol. Exp. Ther., 1988, vol. 245, No. 3, pp. 773–778.
Salituro, et al., *Benzotriazinones as "Virtual Ring" Mimics of o–Methoxybenzamides: Novel and Potent 5–$HT_3$ Receptor Antagonists*, J. Med. Chem., 1990, vol. 33, pp. 2942–2944.
Berger, et al., U.S. patent application Ser. No. 07/704,565.
Berger, et al., U.S. patent application Ser. No. 07/442,082.

Primary Examiner—Richard D. Lovering
Assistant Examiner—Catherine Kilby Scalzo
Attorney, Agent, or Firm—Wayne W. Montgomery; Derek P. Freyberg

[57] ABSTRACT

5-$HT_3$ receptor antagonist compounds of Formula I:

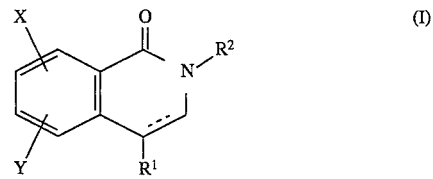

in which

X and Y are independently selected from hydrogen, halogen, hydroxy, lower alkoxy, lower alkyl, nitro, amino, aminocarbonyl, (lower alkyl)amino, di(lower alkyl)amino and (lower alkanoyl)amino;

$R^1$ is hydrogen, lower alkyl, phenyl or halogen;
$R^2$ is a group selected from Formulae (a), (b), (c) and (d):

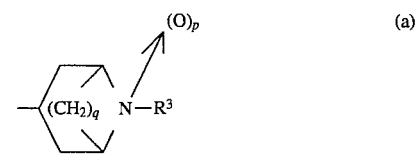

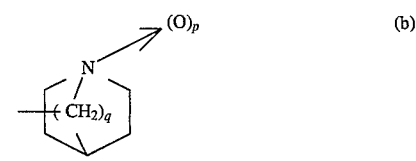

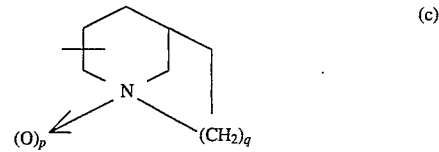

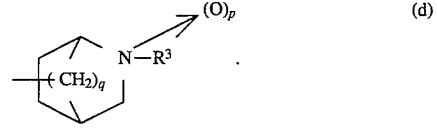

41 Claims, No Drawings

ISOQUINOLINONE AND DIHYDROISOQUINOLINONE 5-HT$_3$ RECEPTOR ANTAGONISTS

FIELD OF THE INVENTION

This invention relates to isoquinolinones and dihydroisoquinolinones which are 5-HT$_3$ receptor antagonists.

BACKGROUND OF THE INVENTION

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. 5-HT Receptors are presently delineated into three major subclassifications - 5-HT$_1$, 5-HT$_2$ and 5-HT$_3$ - each of which may also be heterogeneous. Receptors of the 5-HT$_3$ subclass pervade autonomic neurons and appear to regulate the release of a variety of neurotransmitters in the gastrointestinal, cardiovascular and central nervous systems.

5-HT$_3$ receptors are located in high densities on neurons associated with the emetic reflex and drugs which block the interactions of serotonin at the 5-HT$_3$ receptor level, i.e., 5-HT$_3$ receptor antagonists, possess potent antiemetic properties. Such antagonists demonstrate utility for counteracting the emetic effects of cancer chemotherapy and radiotherapy (see Drugs Acting on 5-Hydroxytryptamine Receptors: *The Lancet* Sep. 23, 1989 and refs. cited therein.).

Functional bowel disorders are prevalent in much of the industrialized world. Chronic gastroesophageal reflux disease alone may be present in as much as 15% of the population. Use of prokinetic agents is one of the most effective methods known for treating such disorders. Because many 5-HT$_3$ antagonists possess prokinetic properties and are relatively free from side effects they are particularly useful in the treatment of gastrointestinal diseases (see Reynolds R. C. Prokinetic Agents: A Key in the Future of Gastroenterology. *Gastroenterology Clinics of North America* 1989; 18: 437–457).

5-HT$_3$ receptors are present in those areas of the brain which control mood, emotion, reward and memory. 5-HT$_3$ receptor antagonists reduce mesolimbic dopamine levels, a necessary property for antipsychotic activity. Such antagonists also increase cholinergic tone in the limbic-cortical region, which may explain their cognitive enhancing effects. In addition, 5-HT$_3$ antagonists possess anxiolytic properties, demonstrate potential for use in the treatment of dependency disorders and are under investigation in patients with schizophrenia (see article from *The Lancet* previously cited).

There is evidence that 5-HT$_3$ receptors mediate nociceptive input to afferent neurons (see Glaum, S., Proudfit, H. K., and Anderson, E. G. 1988; *Neurosci, Lett,* 95, 313). 5-HT$_3$ antagonists may therefore be of value in the control of pain, particularly migraine (see Peatfield R. 1988; Drugs and the Treatment of Migraine. *Trends. Pharmacol. Sci.* 9: 141).

The 5-HT$_3$ receptor antagonist ICS 205–930 inhibits arrhythmias in a variety of animal models and exerts mixed class III and class I antiarrhythmic properties in ventricular myocytes (see Scholtysik, G., Imoto, Y., Yatani, A. and Brown, A. M. 1988; *J. Pharmacol. Exp. Ther.* 245, 773 and references therein). 5-HT$_3$ antagonists may therefore be of use in treating or preventing arrhythmias.

European Patent Application No. 83301158.8, published Nov. 9, 1983 as No. 0 093 488, discloses phthalimidine and dihydroisoquinolinone dopamine receptor antagonists of the formula:

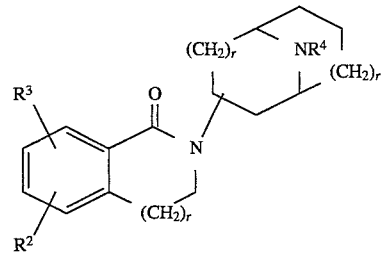

in which, inter alia, R$^2$ and R$^3$ can each be hydrogen, halogen, hydroxy, alkoxy, C$_{1-6}$ alkyl, nitro or amino or aminocarbonyl (which can be substituted by one or two C$_{1-6}$ alkyl, C$_{3-8}$ cycloalkyl or C$_{3-8}$ cycloalkyl(C$_{1-4}$)alkyl) or C$_{1-7}$ acylamino;

r is 1 or 2;

p and q are 0, 1 or 2;

R$^4$ is C$_{1-7}$ alkyl or (CH$_2$)$_s$-R$^6$ where s can be 0 and R$^6$ is C$_{1-6}$ cycloalkyl or (CH$_2$)$_t$R$^7$ where t is 1 or 2, and R$^7$ is phenyl optionally substituted by one or two substituents selected from C$_{1-4}$ alkoxy, trifluoromethyl, halogen, carboxy, esterified carboxy, and C$_{1-4}$ alkyl optionally substituted by hydroxy, C$_{1-4}$ alkoxy, carboxy, esterified carboxy or in vivo hydrolyzable acyloxy or is thienyl; their pharmaceutically acceptable salts, solvates, N-oxides, and their use in treating emesis, impaired gastro-intestinal motility (including ulcers) and CNS disorders (e.g., psychosis) and as analgesics in the treatment of migraine. It further discloses a process for preparing N-substituted dihydroisoquinolinones which involves reacting an azabicycloamine nucleophile (e.g., endo-amino-9-methyl-9-azabicyclo[3.3.1] nonane) with an appropriate homophthalic anhydride, homophthalic acid derivative, or 2-(2-substituted ethyl)benzoic acid derivative (e.g., ethyl 2-(2-bromoethyl)benzoate).

U.S. Pat. No. 4,959,367, issued Sep. 25, 1990, discloses 4-oxobenzotriazine and 4-oxoquinazoline 5-HT$_3$ receptor antagonists of the formula:

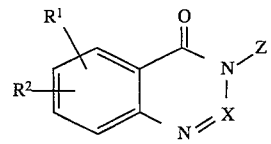

in which

X is N or CH;

R$^1$ and R$^2$ can be, inter alia, hydrogen, halogen, hydroxy, C$_{1-6}$ alkoxy, C$_{1-6}$ alkyl, nitro or amino or aminocarbonyl (which can be substituted by one or two C$_{1-6}$ alkyl, C$_{3-8}$ cycloalkyl or C$_{3-8}$ cycloalkyl(C$_{1-4}$)alkyl) or C$_{1-7}$ acylamino; and Z is a group selected from formula (a), (b) and (c):

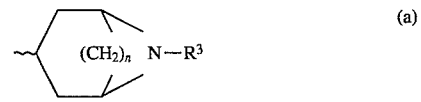

(a)

-continued

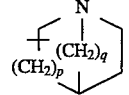
(b)

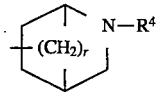
(c)

in which
n is 2 to 3;
p is 1 to 2;
q is 1 to 3;
r is 1 to 3;
and $R^3$ and $R^4$ is $C_{1-4}$ alkyl;

their pharmaceutically acceptable salts and their use in treating emesis (especially emesis caused by cytotoxic agents or radiation induced nausea and vomiting), migraine, cluster headaches, trigeminal neuralgia, visceral pain, arrhythmias, CNS disorders (e.g., anxiety, psychosis, drug withdrawal syndrome, obesity) and gasro-intestinal disorders such as irritable bowel syndrom, retarded gastric emptying, dyspepsia, flatulence, oesophageal reflux and peptic ulcer. It further discloses a process for preparing N-substituted 4-oxoquinazolines which involves reacting an appropriate N-substituted 2-aminobenzamide (e.g., (endo)-N-(8-methyl-8-azabicyclo[3.3.1]oct-3-yl)-2-amino-1-benzamide) with formic acid or triethyl orthoformate.

King, K. D.; Dabbs, S.; Bermudez, J.; Sanger, G. J. *J. Med. Chem.* 1990, 33, 2942–2944 discloses 5-HT$_3$ receptor antagonists of the formula:

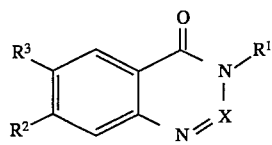

in which
X is N or CH;
$R^1$ is 1-azabicyclo[2.2.2]oct-3-yl or (endo)-8-methyl-8-azabicyclo[3.2.1]oct-3-yl);
$R^2$ is hydrogen, nitro or amino; and
$R^3$ is hydrogen or chlorine. The document further discloses that when X is CH, 5-HT$_3$ receptor potency is substantially reduced.

The disclosures of these and other documents referred to throughout this application, e.g., in the Pharmacology section of the Detailed Description of the Invention, are incorporated herein by reference.

SUMMARY OF THE INVENTION

The first aspect of this invention is the compounds of Formula I:

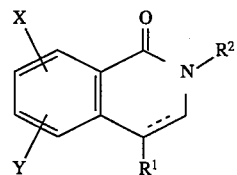
(I)

in which:
X and Y are independently selected from hydrogen, halogen, hydroxy, lower alkoxy, lower alkyl, nitro, amino, aminocarbonyl, (lower alkyl)amino, di(lower alkyl)amino, and (lower alkanoyl)amino;

$R^1$ is hydrogen, lower alkyl, phenyl or halogen;
$R^2$ is a group selected from Formulae (a), (b), (c) and (d):

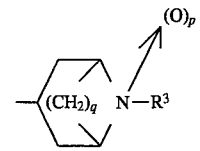
(a)

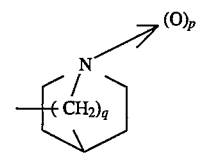
(b)

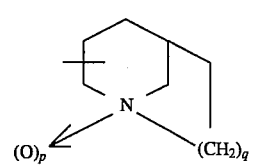
(c)

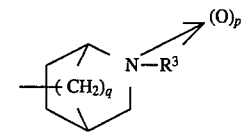
(d)

in which:
p is 0 or 1;
q is 1, 2 or 3; and
$R^3$ is $C_{1-7}$ alkyl, $C_{3-8}$ cycloalkyl, $C_{3-8}$ cycloalkyl-$C_{1-2}$ alkyl, or a group $(CH_2)_t R$ where t is 1 or 2 and $R^4$ is thienyl, pyrrolyl, or furyl, each optionally further substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolyzable acyloxy; and the dashed line denotes an optional bond, except that the bond is present when $R^1$ is halogen or $R^2$ is a group of Formula (a); the pharmaceutically acceptable salts, individual isomers or mixtures of isomers thereof.

A second aspect of this invention is a pharmaceutical composition containing a compound of Formula I in admixture with one or more suitable excipients.

A third aspect of this invention is a method for treating diseases involving emesis, gastrointestinal disorders, CNS disorders, cardiovascular disorders or pain by administering a therapeutically effective amount of a compound of Formula I to a subject in need thereof.

A fourth aspect of this invention is the compounds of Formula II:

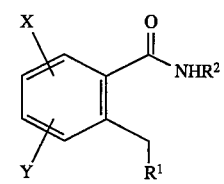
(II)

in which X, Y, $R^1$ and $R^2$ are as defined for Formula I, except that $R^1$ is not halogen, which are useful as intermediates in preparing compounds of Formula I.

A fifth aspect of this invention is the process for preparing compounds of Formula I and is set forth in the "Detailed Description Of The Invention."

DETAILED DESCRIPTION OF THE INVENTION

Definitions

Unless otherwise stated, the following terms used in the specification and claims have the meanings given below:

"Alkyl" means a straight, branched, or cyclic saturated hydrocarbon radical having from one to the number of carbon atoms designated. For example $C_{1-7}$ alkyl is alkyl having at least one but no more than seven carbon atoms, e.g., methyl, ethyl, i-propyl, n-propyl, n-butyl, cyclopropylmethyl, pentyl, cyclohexyl, heptyl and the like.

"Alkoxy" means the radical —OR wherein R is alkyl, e.g., methoxy, ethoxy, i-propoxy, n-propoxy, n-butoxy, pentoxy, hexoxy and the like.

"Alkonyl" means the radical —C(O)R wherein R is alkyl, e.g., ethanoyl, propanoyl, i-butanoyl, n-butanoyl, pentanoyl, hexanoyl and the like.

"Lower" modifies alkyl and refers to those alkyl radicals or R groups in alkoxy and alkonyl radicals containing 1 to 6 carbon atoms.

"Halogen" means fluorine, chlorine, bromine, or iodine.

"Esterified carboxy" means the ester group —COOR wherein R is alkyl.

"In vivo hydrolyzable acyloxy" means a group —OC(O)R, wherein R is alkyl, capable of undergoing enzymatic hydrolysis within a living organism.

"Leaving group" has the meaning conventionally associated with it in synthetic organic chemistry, i.e., an atom or group displaceable under alkylating conditions, and includes halogen and alkane- or arenesulfonyloxy such as mesyloxy, ethanesulfonyloxy, benzenesulfonyloxy, tosyloxy and the like.

"Animal" includes humans, non-human mammals (such as dogs, cats, rabbits, cattle, horses, sheep, goats, swine, and deer) and non-mammals such as birds and the like.

"Cytotoxic agents" include platinum anti-cancer agents such as cisplatin (cis-diamminedichloroplatinum), as well as non-platinum anti-cancer drugs such as cyclophosphamide (cytoxin), vincristrine (leurocristine), procarbazine (N-(1-methylethyl)4-[(2-methylhydrazino)methyl]- benzamide), methotrexate, fluorouracil, mechlorethamine hydrochloride (2-chloro-N-(2-chloroethyl)-N-methylethanamine hydrochloride), doxorubicin, adriamycin, dactinomycin (actinomycin-D) cytarabine, carmustine, dacarbazine, and others listed at page 1143 of the *Journal of Clinical Oncology* 1989; 7(8): 1143.

"Disease" specifically includes any unhealthy condition of an animal or part thereof and includes an unhealthy condition which may be caused by, or incident to, medical or veterinary therapy applied to that animal, i.e., the "side effects" of such therapy. Thus, "disease" here includes the emesis caused by therapy with agents having emetogenic side effects, in particular by therapy for cancer, such as chemotherapy with cytotoxic agents and radiotherapy.

"Emesis", for the purposes of this application, will have a meaning that is broader than the normal, dictionary definition and includes not only vomiting, but also nausea and retching.

"Optional" or "optionally" means that the subsequently described event or circumstance may or may not occur, and that the description includes instances where the event or circumstance occurs and instances in which it does not. For example, "optional bond" means that the bond may or may not be present and that the description includes both single bonds and double bonds; "optionally converting a compound of Formula I to a corresponding pharmaceutically acceptable salt" means that the conversion may or may not be carried out in order for the process described to fall within the invention, and the invention includes those processes wherein the compound of Formula I is converted to the salt and those processes in which it is not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when the acidic proton of X and/or Y hydroxy substituents present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

"Treating" or "treatment" of a disease includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

Compounds that have identical molecular formulae but differ in the nature or sequence of bonding of their atoms or in the arrangement of their atoms in space are termed "isomers". Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diasteromers" and stereoisomers that are mirror images are termed "enantiomers" or sometimes "optical isomers". Stereoisomers that are superimposable upon their mirror images are termed "achiral" and those not superimposable are termed "chiral".

A carbon atom bonded to four different groups is termed a "chiral center" or alternatively an "asymmetric carbon".

When a compound has a chiral center, a pair of enantiomers of opposite chirality is possible. An enantiomer may be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A compound may exist as either an individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of stereochemistry and the separation of stereoisomers are well-known in the art (see discussion in Chapter 4 of "Advanced Organic Chemistry", 3rd edition, March, Jerry, John Wiley and Sons, New York, 1985).

Certain compounds of Formulae I and II may exist as stereoisomers. For example, the $R^2$ substituent described herein may possess a chiral center at the ring carbon which is bonded to the amide nitrogen. In addition, compounds of Formula I wherein the optional bond is absent and $R^1$ is lower alkyl possess a chiral center at the 4-position. Finally, compounds of Formula I may exist as the endo or exo form, e.g., when the $R^2$ substituent is 1-azabicyclo[3.3.1]non-4-yl.

When a compound of Formula I or II possesses one chiral center, a pair of enantiomers exists. When two chiral centers are present in a compound of Formula I, four separate steroisomers exist (i.e., two separate pairs of enantiomers). When a compound of Formula I possesses two chiral centers and may exist as endo or exo, eight separate stereoisomers are possible (i.e., two separate pairs of enantiomers in the endo or exo form).

It is to be understood that when referring to Formulae I and II or Formulae (b), (c) and (d) in this application, a straight line depicting the covalent bond between the asymmetric carbon and the amide nitrogen represents either the R or S configuration or a mixture, racemic or otherwise, thereof. Similarly, when referring to Formula I wherein the optional bond is absent, a straight line depicting the covalent bond between the asymmetric carbon and the $R^1$ substituent represents either the R or S configuration or a mixture, racemic or otherwise, thereof. For purposes of the present application when referring to a compound by name or by formula and the configuration is not designated, it is to be understood that the reference is to all possible forms.

Certain $R^2$ substituents described in this application are of particular interest and are therefore defined specifically. These $R^2$ substituents of particular interest are as follows:

(1) Formula (b) where q is 2 and p is 0 having the specific formula

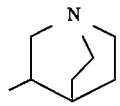

is referred to as 1-azabicyclo[2.2.2]oct-3-yl;

(2) Formula (b) where q is 2 and p is 0 having the specific formula

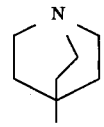

is referred to as 1-azabicyclo[2.2.2]oct-4-yl;

(3) Formula (a) where q is 3, p is 0 and $R^3$ is methyl having the specific formula

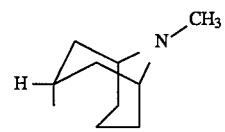

is referred to as endo-9-methyl-9-azabicyclo[3.3.1]non-3-yl;

(4) Formula (a) where q is 3, p is 0 and $R^3$ is methyl having the specific formula

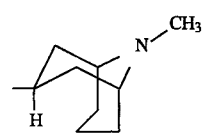

is referred to as exo-9-methyl-9-azabicyclo[3.3.1]non-3-yl;

(5) Formula (a) where q is 2, p is 0 and $R^3$ is methyl having the specific formula

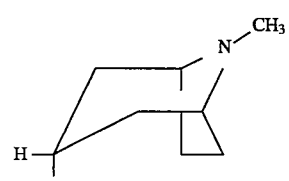

is referred to as endo-8-methyl-8-azabicyclo[3.2.1]oct-3-yl;

(6) Formula (a) where q is 2, p is 0 and $R^3$ is methyl having the specific formula

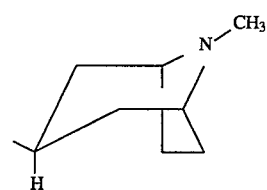

is referred to as exo-8-methyl-8-azabicyclo[3.2.1]oct-3-yl;

(7) Formula (c) wherein q is 2 and p is 0 having the specific formula

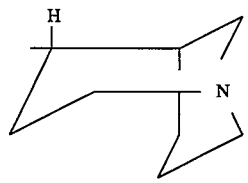

is referred to as endo-1-azabicyclo[3.3.1]non-4-yl; and (8) Formula (c) wherein q is 2 and p is 0 having the specific formula

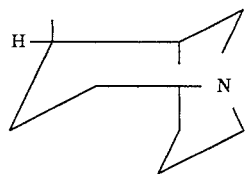

is referred to as exo-1-azabicyclo[3.3.1]non-4-yl.

Compounds of Formulae I and II are named in accordance with generally acceptable nomenclature rules established by the International Union of Pure and Applied Chemistry and numbered as shown below. For example, the compound of Formula I wherein the optional bond is present, X, Y and $R^1$ are hydrogen and $R^2$ is 1-azabicyclo[2.2.2.]oct-3-yl

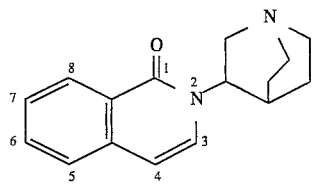

is named 2-(1-azabicyclo[2.2.2.]oct-3-yl)-1(2H)-isoquinolinone.

The compound of Formula II wherein X, Y and $R^1$ are hydrogen and $R^2$ is 1-azabicyclo[2.2.2]oct-3-yl

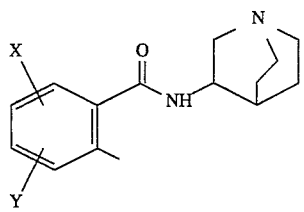

is named N-(1-azabicyclo[2.2.2]oct-3-yl)-2-methylbenzamide.

Presently Preferred Compounds

While the broadest definition of this invention is as set forth in the Summary of the Invention, certain compounds of Formulae I and II are preferred. For example, preferred compounds of Formula I are those in which X and Y are independently selected from hydrogen, lower alkyl, lower alkoxy and halogen, $R^1$ is hydrogen, lower alkyl, phenyl or halogen and $R^2$ is one of the following groups:

1-azabicyclo[2.2.2]oct-3-yl;
1-azabicyclo[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

Of particular interest are those compounds of Formula I in which X is hydrogen, lower alkyl, lower alkoxy or halogen, Y is hydrogen, $R^1$ is hydrogen, lower alkyl or phenyl and $R^2$ is 1-azabicyclo[2.2.2]oct-3-yl.

Of most interest are compounds of Formula I in which X is lower alkyl or lower alkoxy, Y and $R^1$ are hydrogen, and $R^2$ is 1-azabicyclo[2.2.2]oct-3-yl, in particular those compounds in which $R^2$ is (S)-1-azabicyclo[2.2.2]oct-3-yl. Representative compounds are made by following the procedures set out in Examples 2, 3 and 4.

It is understood that these compounds of Formula I of special interest are particularly useful in the pharmaceutical compositions and methods of treatment of this invention.

Preferred compounds of Formula II are those in which X and Y are independently selected from hydrogen, lower alkyl, lower alkoxy and halogen, $R^1$ is hydrogen, lower alkyl or phenyl, and $R^2$ is one of the following groups:

1-azabicyclo[2.2.2]oct-3-yl;
1-azabicyclo[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

Of particular interest are those compounds of Formula II in which X is hydrogen, lower alkyl, lower alkoxy or halogen, Y is hydrogen, $R^1$ is hydrogen, lower alkyl or phenyl, and $R^2$ is 1-azabicyclo[2.2.2]oct-3-yl.

Of most interest are compounds of Formula II in which X is lower alkyl or lower alkoxy, Y and $R^1$ are hydrogen, and $R^2$ is 1-azabicyclo[2.2.2]oct-3-yl, in particular the S-isomers thereof. Representative compounds are made by following the procedures set out in Example 1.

It is understood that these compounds of Formula II of special interest are particularly useful in the synthesis of preferred compounds of Formula I.

Utility

Compounds of Formula I exhibit utility in treating a broad range of diseases in animals, particularly humans. Examples of diseases that may be treated using the compounds of Formula I include emesis, gastrointestinal disorders, central nervous system (CNS) disorders, cardiovascular disorders or pain.

Compounds of Formula I are useful in the prevention and treatment of emesis. Causes of such emesis include surgical anesthesia, psychological stress, pregnancy, certain disease states, radiotherapy, radiation poisoning and toxic substances. Disease states which are known to induce emesis include conditions such as gut obstruction, raised intracranial pressure, acute myocardial infarction, migraine headaches and adrenal crisis. Toxic substances which induce emesis include toxins in the form of abnormal metabolites or abnormal accumulation of natural occurring substances associated with such conditions as hepatic coma, renal failure, diabetic ketoacidosis, hyperthyroid crisis, both hypo- and hyperparathyroidism and Addison's disease. Emesis may also be caused by ingested toxins, e.g., enterotoxins in staphylococcus-contaminated foods, or by drugs administered for therapeutic purposes, e.g., digitalis, emetine and chemotherapeutic agents.

Compounds of Formula I are of particular value in treating (especially preventing) the emesis induced by radiation poisoning, treatment for cancer with radiotherapy or chemotherapy with cytotoxic agents or drug therapy in general wherein a significant side effect is emesis, e.g., amphotericin B in treating immunosuppressed patients, zidovudine (AZT) in the treatment of AIDS and interleukin in treating cancer.

Compounds of Formula I are useful as prokinetic agents in the treatment of gastrointestinal diseases, i.e., diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome and retarded gastric emptying. The compounds of Formula I are also useful as short-term prokinetics to facilitate diagnostic radiology and intestinal incubation. In addition, the compounds are useful for treating diarrhea, particularly diarrhea induced by cholera and carcinoid syndrome.

Compounds of Formula I are useful in treating diseases of the central nervous system. Categories of such diseases include cognitive disorders, psychoses, obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses that are treatable using the compounds of Formula I include paranoia, schizophrenia and autism. Representative, treatable anxiety/depressive states include anticipatory anxiety (e.g., prior to surgery, dental work, etc.), depression, mania, convulsions and anxiety caused by withdrawal from addictive substances such as opiates, benzodiazapines, nicotine, alcohol, cocaine and other drugs of abuse.

Compounds of Formula I are useful in the treatment of cardiovascular diseases. Such diseases include arrhythmias and hypertension.

It is thought that $5\text{-HT}_3$ antagonists prevent certain adverse nervous transmissions and/or prevent vasodilation and are therefore of value for reducing perceived levels of pain. Compounds of Formula I are, therefore, useful in treating pain such as that associated with cluster headaches, migraines, trigeminal neuralgia and visceral pain (e.g., that caused by abnormal distension of hollow visceral organs).

In summary, an aspect of this invention is a method for treating an animal, particularly a human, exhibiting a disease involving emesis, a gastrointestinal disorder, a CNS disorders, a cardiovascular disorder or pain by administering a therapeutically effective amount of a compound of Formula I to such animal.

Pharmacology $5\text{-HT}_3$ Receptor binding affinity is measured at $5\text{-HT}_3$ receptors in membranes prepared from the cerebral cortex of rat brains, an accepted in vitro assay (e.g., see Kilpatrick, G. J., Jones, B. J. and Tyers, M. B., *Nature* 1987; 330: 24–31). The $5\text{-HT}_3$ receptor binding assay, as adapted for testing compounds of Formula I, is described in detail by Example 6 of this application. The compounds of Formula I exhibit affinity for the $5\text{-HT}_3$ receptor in this assay.

$5\text{-HT}_3$ receptor antagonist activity is measured by the ability of compounds to inhibit the yon Bezold-Jarisch reflex in anesthetized rats, an accepted in vivo assay (e.g., see Butler, A., Hill, J. M., Ireland, S. J., Jordan, C. C., Tylers, M. B., *Brit. J. Pharmacol.* 1988; 94: 397–412; Cohen, M. L., Bloomquist, W., Gidda, J. S., Lacefield, W., *J. Pharmacol. Exp. Ther.* 1989; 248: 197–201; Fozard, J. R., MDL 72222: *Arch. Pharmacol.* 1984; 326: 36–44). The $5\text{-HT}_3$ receptor antagonist assay, as adapted for testing compounds of Formula I, is described in detail by Example 7 of this application.

Anti-emetic activity is determined by measuring reduction of cisplatin-induced emesis in ferrets, an accepted assay (e.g., Costall, B., Domeney, A. M., Naylor, R. J., and Tattersall, F. D., *Neuropharmacology* 1986; 25(8): 959–961; Miner, W. D. and Sanger G. J., *Brit. J. Pharmacol.* 1986; 88: 497–499). The ferret, anti-emetic assay, as adapted for testing compounds of Formula I, is described in detail by Example 8 of this application.

Anti-emetic activity is also determined by measuring reduction of cisplatin-induced emesis in dogs, an accepted assay (e.g., see Smith, W. L., Alphin, R. S., Jackson, C. B., and Sancilio, L. F., *J. Pharm. Pharmacol.* 1989; 41: 101–105; Gylys, J. A., *Res. Commun. Chem. Pathol Pharmacol.* 1979; 23(1): 61–68). The dog, anti-emetic assay, as adapted for testing compounds of Formula I, is described in detail by Example 9 of this application.

Prokinetic activity is determined by measuring the rate of gastric emptying after oral administration of test meal to rats, an accepted in vivo assay (e.g., see Droppleman, D., Gregory, R., and Alphin, R. S., *J. Pharmacol. Methods* 1980; 4(3): 227–30). The prokinetic assay is described in detail by Example 10 of this application.

Anxiolytic activity is determined by the art-recognized Crawley and Goodwin two-compartment exploratory model (e.g., see Kilfoil, T., Michel, A., Montgomery, D., and Whiting, R. L., *Neuropharmacology* 1989; 28(9): 901–905). In brief, the method involves determining whether a compound reduces the natural anxiety of mice in a novel, brightly lighted area. The anxiolytic behavior assay is described in detail by Example 11 of this application.

Anxiolytic activity during withdrawal from drugs of abuse is determined by the mouse, withdrawal anxiety test, an accepted assay (e.g., see Carboni, E., Acquas, E., Leone, P., Perezzani, L., and Di Chiara, G., *Eur. J. Pharmacol* 1988; 151: 159–160). This procedure utilizes the exploratory model described above to test for anxiolytic activity after chronic administration and subsequent abrupt cessation of ethanol, cocaine or nicotine treatments. The withdrawal anxiety assay is described in detail by Example 12 of this application.

Cognition enhancing activity is determined by the mouse, habituation/cognitive enhancement test (e.g., see Barnes, J. M., Costall, B., Kelly, M. E., Naylor, F. J., Onaivi, E. S., Tomkins, D. M. and Tyers, M. B., *Br. J, Pharmacol.* 1989; 98: 693P). This procedure utilizes the exploratory model described above to test for improvements in the impaired cognitive performance of aged mice. The cognitive enhancement assay is described in detail by Example 13 of this application.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from approximately 1.0 nanogram per Kg (ng/Kg) body weight per day to 1.0 mg/Kg body weight per day.

Preferably the amount will be approximately 10 ng/Kg/day to 0.1 mg/Kg/day. Therefore, a therapeutically effective amount for a 70 Kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso 1985. *Remington's Pharmaceutical Sciences.* 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001% w to 1.0% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 5 of this application.

Processes for Preparing Compounds of the Invention

Compounds of Formula I are prepared by the reaction sequence shown below in Scheme I:

Scheme I

Step 1

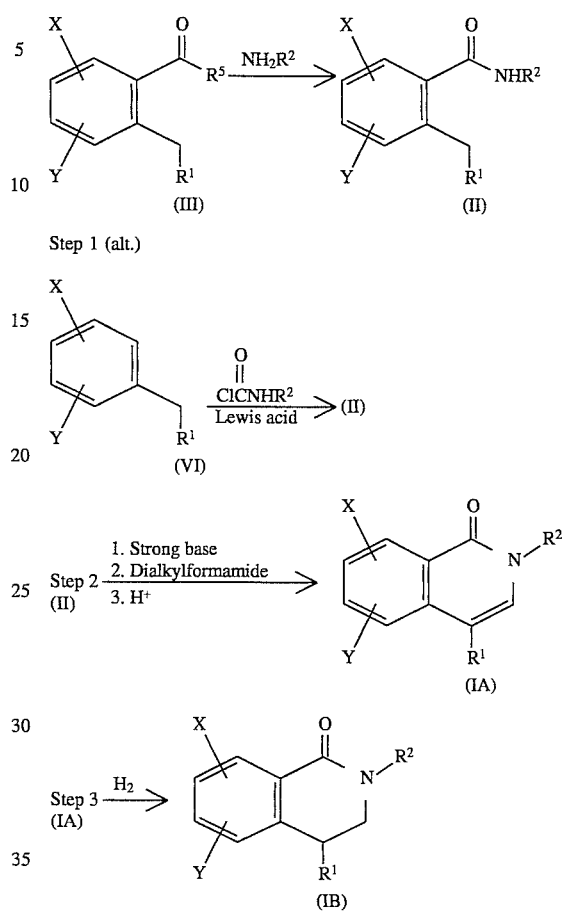

wherein $R^5$ is hydroxy, lower alkoxy or halogen and X, Y, $R^1$ and $R^2$ are as defined in the Summary of the Invention, except that $R^1$ of Formula II or III is not halogen, with the processes applying particularly well to the presently preferred compounds.

Scheme I

Compounds of Formula I are prepared by a two step synthesis comprising (1) converting an acid or acid derivative of Formula III or an alkylbenzene of Formula VI to a substituted amide of Formula II and (2) reacting the amide with a formylating agent in the presence of a strong base and then acidifying to form an isoquinolinone of Formula IA (compounds of Formula I in which the optional bond is present). Dihydroisoquinolinones of Formula IB (compounds of Formula I in which the optional bond is absent) are subsequently prepared by reduction.

Step 1

Compounds of Formula II are prepared by reacting a compound of Formula III with a substituted amine of the formula $NH_2R^2$ in which $R^2$ is as defined in the Summary of the Invention. The reaction is carried out at 20° C. to 200° C. and ambient pressure for 0.5 to 3 hours in a suitable solvent. Representative, suitable solvents include methylene chloride, THF and toluene. The conversion of a benzoic acid of Formula III to the corresponding amide of Formula II is described in detail in Method A of Example 1. The conversion of a methyl benzoate of Formula III to the corresponding amide of Formula II is described in detail in Method B of Example 1.

Alternatively, compounds of Formula II may be prepared by Friedel-Crafts acylation in which a chloroformamide of the formula ClC(O)NHR² is reacted with an alkylbenzene of Formula VI in the presence of a Lewis acid such as aluminum chloride, boron trifluoride, hydrogen fluoride or phosphoric acid.

In general, the starting materials utilized in the preparation of compounds of Formula II are known to or can readily be synthesized by those of ordinary skill in the art. For example, the compound of Formula III wherein X, Y and $R^1$ are hydrogen, namely o-toluic acid, is commercially available or may be prepared by reacting toluene with acetyl chloride in the presence of a Lewis acid such as aluminum chloride, boron trifluoride, hydrogen fluoride or phosphoric acid.

Step 2

Compounds of Formula IA are prepared by reacting amides of Formula II with a dialkylformamide in the presence of a strong base and than acidifying. The reaction is carried out in a suitable solvent at at temperatures ranging from −70° C. to 25° C. under an inert atmosphere (e.g., argon or nitrogen, preferably nitrogen) and ambient pressure. Suitable solvents include ethers such as diethyl ether, dimethoxyethane or tetrahydrofuran (THF). The dialkylformamide, preferably dimethylformamide (DMF), is generally used in molar excess relative to the amide of Formula II. Any strong base, such as a Grignard reagent or an appropriate alkyllithium, preferably n-butyllithium, can be utilized. Step 2 of Scheme I is described in detail in Example 2.

Compounds of Formula IB may be prepared by reduction of the corresponding compound of Formula IA. The reduction is carried out under standard hydrogenation conditions with an appropriate hydrogenation catalyst and in a suitable polar, organic solvent. Reaction pressures may vary from atmospheric to approximately 15 megaPascals (mPa) and temperatures may range from ambient to approximately 100° C. While any standard catalyst (e.g., rhodium on alumina, etc.) may be used, certain catalysts are preferred. Preferred catalysts include 10% palladium hydroxide, 20% palladium hydroxide on carbon, Pearlman's catalyst (50% H₂O - 20% palladium content) and palladium/BaSO₄. Suitable solvents include ethanol, DMF, acetic acid, ethyl acetate, tetrahydrofuran, toluene, and the like.

Depending upon the catalyst, solvent, pressure and temperature chosen, the reduction process may take from a few hours to a few days to complete. As an example, a reaction carried out with 20% palladium hydroxide in acetic acid and 70% perchloric acid at 15 kPa and 85° C. takes approximately 24 hours for full reduction to occur. The reduction of a compound of Formula IA to a compound of Formula IB is described in detail in Example 3.

A compound of Formula IA can be reduced in either the nonsalt or salt form. If an optically active reagent is employed to form the salt of a compound of Formula IA and reduction of the salt form results in the formation of a chiral center at the 4-position, i.e., when $R^1$ is lower alkyl, formation of one enantiomer over the other may be favored.

Compounds of Formula I are also prepared by the reaction sequence shown below in Scheme II.

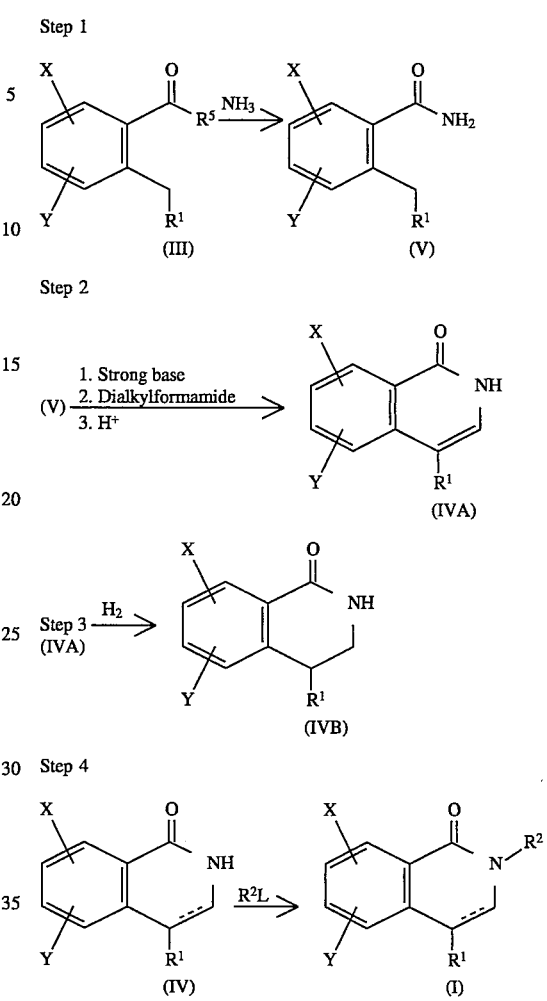

Scheme II in which $R^5$ is hydroxy, lower alkoxy or chloride, L is a leaving group and X, Y, $R^1$ and $R^2$ are as defined in the summary of the Invention, except that $R^1$ of Formula III or V is not halogen, with the processes applying particularly well to the presently preferred embodiments.

Scheme II

Alternatively, compounds of Formula I are prepared by a three step synthesis comprising (1) converting an acid or acid derivative of Formula III to an unsubstituted amide of Formula V, (2) reacting the amide with a formylating agent in the presence of a strong base and then acidifying to form an isoquinolinone of Formula IVA (a compound of Formula IV in which the optional bond is present), (3) optionally reducing a compound of Formula IVA to a dihydroisoquinolinone of Formula IVB (a compound of Formula IV in which the optional bond is absent) and (4) condensing the compound of Formula IV with an appropriate alkylating agent to form a compound of Formula I.

Step 1

Compounds of Formula V may be prepared by proceeding as in Step 1 of Scheme I but replacing the substituted amine with ammonia.

Step 2

Compounds of Formula IVA may be prepared by proceeding as in Step 2 of Scheme I but substituting a compound of Formula V for the compound of Formula II. Compounds of Formula IVB may be prepared by proceeding as described above for the hydrogenation of a compound of Formula IA but substituting a compound of Formula IVA.

Step 3

Compounds of Formula I may be prepared by reacting, in the presence of a strong base, a compound of Formula IV with an alkylating agent of the formula $R^2L$ wherein $R^2$ is as defined in the Summary of the Invention and L is a leaving group. The reaction is carried out under standard amide alkylating conditions (Luh, T. and Fung S. H., Synth. Commun. (1979), 9, 757) in an inert solvent at a reaction temperature of 20° C. to 100° C. Appropriate bases include sodium or sodium hydride and are usually employed in molar excess. Suitable solvents include tetrahydrofuran or N,N-dialkylformamides such as N,N-dimethylformamide.

Alternatively, alkylation may be accomplished via phase-transfer catalyst (PTC) techniques. Such techniques comprise carrying out the reaction in the presence of catalyst and in a liquid-liquid two phase solvent system (Gajda, T. and Zwierzak, A., Synthesis, Communications (1981), 1005), or preferably, in a solid-liquid system (Yamawaki, J., Ando, T. and Hanafusa, T., Chem, Lett. (1981), 1143; Koziara, A., Zawaszki, S. and Zwierzak, A., Synthesis (1979) 527, 549).

A liquid-liquid two-phase system is comprised of an aqueous phase consisting of a concentrated alkali hydroxide solution (e.g., 50% aqueous sodium hydroxide), an organic phase comprised of an inert water-immiscible organic solvent solvent, and an appropriate catalyst. A solid-liquid system consists of a powdered alkali hydroxide/alkali carbonate suspended in an organic solvent and catalyst.

The reaction is effected by adding slowly to a PTC system containing a compound of Formula IV an alkylating agent of the formula $R^2L$ until 10 to 50% in excess. The reaction mixture is kept at reflux until the reaction is complete. The mixture is then cooled to room temperature and the compound of Formula I is isolated by conventional methods. Suitable organic solvents include benzene, toluene, and the like. Appropriate catalysts include alumina coated with potassium fluoride and quaternary ammonium sulfates such as tetra-n-butylammonium hydrogen sulfate and tricaprylylmethylammonium chloride.

A variation of Scheme II comprises converting a compound of Formula V to a compound of Formula II by one of the above described alkylation processes and then proceeding as in Step 2 of Scheme I to form a compound of Formula I.

Additional Processes

Compounds of Formula I in which substituents X and/or Y are $NH_2$ may be prepared by the reduction of a nitro substituent on the corresponding compound of Formula I; wherein X and/or Y are alkoxy or dialkylamino, by substitution of a corresponding nitro or halo substituent; or wherein X and/or Y is hydroxy, by the de-alkylation of a corresponding alkoxy substituent. Furthermore, compounds of Formula I wherein Y is Cl, Br, I or $NO_2$ may be prepared by the introduction of such substituent onto a ring activated by a X substituent such as $NH_2$, NHR, $NR_2$, OH or alkoxy; or wherein X and/or Y is an acetamido substituent, by the acylation of a corresponding amino substituent. All of the additional processes described above may be performed by methods well known to one of ordinary skill in the art of organic synthesis.

Compounds of Formula I in which $R^1$ is fluorine, chlorine, bromine or iodine may be prepared by reacting a 1(2H)-isoquinolinone of Formula I with the appropriate halogen. The preparation of a compound of Formula I in which $R^1$ is bromine is described in detail in Example 4.

Compounds of Formula I wherein p is 1 (compounds of Formula I wherein the cyclic amine portion of $R^2$ is in the N-oxide form) may be prepared by oxidation of the corresponding compound of Formula I wherein p is 0, preferably nonsalt form. The oxidation is carried out at a reaction temperature of approximately 0° C. with an appropriate oxidizing agent and in a suitable inert, organic solvent. Suitable oxidizing agents include peroxy acids such as trifluoroperacetic acid, permaleic acid, perbenzoic acid, peracetic acid, and m-chloroperoxybenzoic acid. Suitable solvents include halogenated hydrocarbons, e.g., dichloromethane. Alternatively, the compounds of Formula I wherein p is 1 may be prepared using N-oxide derivatives of the starting materials or intermediates, which may be prepared in a similar manner.

Compounds of Formula I wherein p is 0 (compounds of Formula I wherein the cyclic amine portion of $R^2$ is not in the N-oxide form) are also prepared by reduction of the corresponding compound of Formula I wherein p is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triaryl phosphines (e.g., triphenyl phosphine), alkali borohydrides (e.g., lithium borohydride, sodium borohydride, etc.), phosphorus trichloride and tribromide. Suitable solvents include acetonitrile, ethanol or aqueous diozane.

As will be apparent to one of ordinary skill in the art, compounds of Formula I may be prepared as individual isomers or mixtures of isomers. Isomers which are diastereomers have distinct physical properties (e.g., melting points, boiling points, solubilities, reactivity, etc.) and are readily separated by taking advantage of these dissimilarities. For example, diastereomers can be separated by chromatography or, preferably, by separation/resolution techniques based upon differences in solubility. Optical isomers can be separated by reacting the racemic mixture with an optically active resolving agent to form a pair of diastereomeric compounds. The isomers are then separated by any of the techniques described above for the separation of diastereomers and the pure optical isomer recovered, along with the resolving agent, by any practical means that would not result in racemization. While resolution of optical isomers can be carried out using covalent diastereomeric derivatives of compounds of Formula I, dissociable complexes are preferred, e.g., crystalline diastereomeric salts. Suitable resolving acids include tartaric acid, o-nitrotartranilic acid, mandelic acid, malic acid, the 2-arylpropionic acids in general, and camphorsulfonic acid.

Individual isomers of compounds of Formula I can also be separated by such methods as direct or selective crystallization or by any other method known to one of ordinary skill in the art. A more detailed description of the techniques applicable to the resolution of stereoisomers of compounds of Formula I can be found in Jean Jacques, Andre Collet, Samuel H. Wilen, Enantiomers, Racemates and Resolutions, John Wiley & Sons, Inc. (1981). Alternatively, individual isomers of compounds of Formula I can be prepared using the isomeric forms of the starting materials.

Compounds of Formula I are be converted to the corresponding acid addition salt with a pharmaceutically acceptable inorganic or organic acid. In addition, pharmaceutically acceptable salts may be formed when the acidic proton of X and/or Y hydroxy substituents present are capable of reacting with inorganic or organic bases. Inorganic and organic acids and bases suitable for the preparation of the pharmaceutically acceptable salts of compounds of Formula I are set forth in the definitions section of this application.

Compounds of Formula I in the acid addition salt form are converted to the corresponding free base by treatment with a suitable base such as ammonium hydroxide solution, sodium hydroxide or the like. Compounds of Formula I in which X and/or Y hydroxy substituents form salts are converted to the corresponding free base by treatment with a suitable acid such as hydrochloric acid.

Of the two processes for synthesizing compounds of Formula I described within this application, Scheme I is preferred. While compounds of Formula I may be synthesized by the process described in Scheme II, the alkylation step therein may require severe reaction conditions and is usually restricted to alkylation of unsubstituted amides with primary alkylating agents, e.g., $CH_3L$.

In summary, the processes for preparing the compounds of Formula I are (1) reacting an compound of Formula II with a dialkylformamide in the presence of a strong base and then acidifying to form a compound of Formula IA or reacting a compound of Formula IV with an alkylating agent of the formula $R^2L$ to form a compound of Formula I;

(2) optionally hydrogenating a compound of Formula IA to form a compound of Formula IB;

(3) optionally reacting with or exchanging substituents present on a compound of Formula I to form an additional substituted compound of Formula I.

(4) optionally converting a salt of a compound of Formula I to a corresponding compound of Formula I;

(5) optionally converting a compound of Formula I to a corresponding pharmaceutically acceptable salt;

(6) optionally oxidizing a compound of Formula I wherein p is 0 to the corresponding N-oxide wherein p is 1;

(7) optionally reducing the N-oxide of a compound of Formula I wherein p is 1 to the corresponding compound of Formula I wherein p is 0; or (8) optionally separating a mixture of isomers of a compound of Formula I into a single isomer.

In any of the above processes, a reference to Formula I, II, III, IV, V or VI refers to such Formula wherein X Y $R^1$, $R^2$, $R^3$, $R^4$, $R^5$, p, q and t have the broadest definitions set forth in the Summary of the Invention, except that $R^1$ of Formula II, III, IV or V is not halogen, with the processes applying particularly well to the presently preferred embodiments.

EXAMPLE 1

Method A (RS)-N-(1-azabicyclo[2.2.2]oct-3-yl)-2,3-dimethylbenzamide

The following is the preparation of a compound of Formula II via Scheme I, Step 1 in which the optional bond is present;
X is methyl in the 3-position;
Y is hydrogen;
$R^1$ is hydrogen; and
$R^2$ is (RS)-1-azabicyclo[2.2.2]oct-3-yl.

2,3-dimethylbenzoic acid (5.0 g; 33.3 mmol), oxalyl chloride (40.0 mmol, 3.5 mL) and dimethylformamide (0.1 mL) were dissolved in methylene chloride (100 mL). The mixture was stirred at room temperature for 1 hour and then concentrated under reduced pressure. A solution of the concentrate in toluene (100 mL) was added dropwise to a stirred solution of (RS)-3-amino-1-azabicyclo[2.2.2]octane dihydrochloride (7.0 g; 35 mmol) in toluene (50 mL) and NaOH (2.0N, 50 mL) at 0° C. The reaction mixture was maintained at 0° C. and stirred for 30 minutes. The aqueous layer was extracted with of toluene (2×50 mL) and the combined organic layers dried over magnesium sulfate. Removal of the solvent under reduced pressure gave (RS)-N-(1-azabicyclo[2.2.2]oct-3-yl)-2,3-dimethylbenzamide as a white solid (5.5 g, 25.4 mmol), m.p. 160°–161° C. The hydrochloride salt is prepared from ethanol-hydrogen chloride.

Proceeding as in Example 1, Method A, but replacing (RS)-3-amino-1-azabicyclo[2.2.2]octane with (S)-3-amino-1-azabicyclo[2.2.2]octane gave (S)-N-(1-azabicyclo[2.2.2]oct-3-yl)-2,3-dimethylbenzamide hydrochloride, m.p. 263°–265° C., $[\alpha]_D^{25}$ −16° (c=0.18, $H_2O$).

Proceeding as in Example 1, Method A, but replacing 2,3-dimethylbenzoic acid with 3-chloro-2-methylbenzoic acid and (RS)-3-amino-1-azabicyclo[2.2.2]octane with (S)-3-amino-1-azabicyclo[2.2.2]octane gave (S)-N-(1-azabicyclo[2.2.2]oct-3-yl)-3-chloro-2-methylbenzamide.

Proceeding as in Example 1, Method A, but replacing 2,3-dimethyl benzoic acid with 2-butylbenzoic acid gave (RS)-N-(1-azabicyclo[2.2.2]oct-3-yl-2-methylbenzamide hydrochloride, m.p. 230°–231° C.

Proceeding as in Example 1, Method A, but replacing 2,3-dimethyl benzoic acid with 2-benzylbenzoic acid, gave (RS)-N-(1-azabicyclo[2.2.2]oct-3-yl)-2-benzylbenzamide, m.p. 187°–188° C.

Proceeding as in Example 1, Method A, but replacing 2,3-dimethyl benzoic acid with 2-benzylbenzoic acid and (RS)-3-amino-1-azabicyclo[2.2.2]octane with (S)-3-amino-1-azabicyclo[2.2.2]octane gave (S)-N-(1-azabicyclo[2.2.2]oct-3-yl)-2-benzylbenzamide.

Proceeding as in Example 1, Method A, but replacing 2,3-dimethyl benzoic acid with 2-butylbenzoic acid and (RS)-3-amino-1-azabicyclo[2.2.2]octane with (S)-3-amino-1-azabicyclo[2.2.2]octane gave (S)-N-(1-azabicyclo[2.2.2]oct-3-yl)-2-butylbenzamide.

Method B (S)-N-(1-azabicyclo[2.2.2]oct-3-yl)-3-methoxy-2-methylbenzamide

The following is the preparation of a compound of Formula II via Scheme I, Step 1 in which
the optional bond is present;
X is methoxy in the 3-position;
Y is hydrogen;
$R^1$ is hydrogen; and
$R^2$ is (S)-1-azabicyclo[2.2.2]oct-3-yl.

A solution of trimethylaluminum (0.8 mmol) in toluene was slowly added to a solution of (S)-3-amino-1-azabicyclo[2.2.2]octane (0.1 g; 0.8 mmol) in toluene (5.0 mL) and the mixture stirred for 15 minutes. A solution of methyl 3-methoxy-2-methylbenzoate (0.1 g; 0.55 mmol) in toluene (2 mL) was added and the reaction mixture heated to reflux until, as indicated by thin-layer chromatography, the reaction had finished. The mixture was cooled to 0° C. and then carefully quenched with water (0.4 mL). The reaction mixture was stirred for an additional 30 minutes and then filtered washing with ethyl acetate (2×20 mL). Removal of the solvent from the combined filtrate gave (S)-N-(1-azabicyclo[2.2.2]oct-3-yl)-3-methoxy-2-methylbenzamide as a white solid (0.19 g, 0.686 mmol). Preparation of the hydrochloride salt from ethanol-hydrogen chloride gave (S)-N-(1-azabicyclo[2.2.2]oct-3-yl)-3-methoxy-2-methylbenzamide hydrochloride, m.p. 259°–261° C., $[\alpha]_D^{25}$ –13.8° (c=0.16, H$_2$O).

Proceeding as in Example 1, Method B, but replacing methyl 3-methoxy-2-methylbenzoate with methyl 3-ethyl-2-methylbenzoate gave (S)-N-(1-azabicyclo[2.2.2]oct-3-yl)-3-ethyl-2-methylbenzamide hydrochloride.

Proceeding as in Example 1, Method B, but replacing (S)-3-amino-1-azabicyclo[2.2.2]octane with endo-8-methyl-8-azabicyclo[3.2.1]octane gave endo-N-(8-methyl-8-azabicyclo[3.2.1]oct-3-yl)-3-methoxy-2-methylbenzamide.

Proceeding as in Example 1, Method B, but replacing methyl 3-methoxy-2-methylbenzoate with ethyl 2-ethyl-3-methylbenzoate and (S)-3-amino-1-azabicyclo[2.2.2]octane with (RS)-3-amino-1-azabicyclo[2.2.2]octane gave (RS)-N-(1-azabicyclo[2.2.2]oct-3-yl)-2-ethyl-3-methylbenzamide, m.p. 125° C.

Proceeding as in Example 1, Method A or B, the following are prepared:

N-(1-azabicyclo[2.2.2]oct-4-yl)-2-methylbenzamide;

endo-N-(9-methyl-9-azabicyclo[3.3.1]non-3-yl)-2-methylbenzamide;

exo-N-(9-methyl-9-azabicyclo[3.3.1]non-3-yl)-2-methylbenzamide;

endo-N-(8-methyl-8-azabicyclo[3.2.1]oct-3-yl)-2-methylbenzamide;

exo-N-(8-methyl-8-azabicyclo[3.2.1]oct-3-yl)-2-methylbenzamide;

endo-N-(1-azabicyclo[3.3.1]non-4-yl)-2-methylbenzamide; and exo-N-(1-azabicyclo[3.3.1]non-4-yl)-2-methylbenzamide.

EXAMPLE 2

(S)-2-(1-azabicyclo[2.2.2]oct-3-yl)-5-methoxy-1(2H)-isoquinolinone

The following is the preparation of a compound of Formula via Scheme I, Step 2 in which the optional bond is present;

X is methoxy in the 5-position;

Y is hydrogen;

R$^1$ is hydrogen; and

R$^2$ is (S)-1-azabicyclo[2.2.2]oct-3-yl.

A solution of n-butyllithium (2.2 mmol) in hexane was added in a dropwise fashion to a stirred solution of (S)-N-(1-azabicyclo[2.2.2]oct-3-yl)-3-methoxy-2-methylbenzamide (0.24 g, 0.87 mmol), from Example 1, Method B, in dry tetrahydrofuran (1.0 mL) at −70° C. The mixture was maintained at −10° C. and stirred for 1 hour. The mixture was then cooled to −70° C. and dimethylformamide (0.1 mL) added. The reaction mixture was allowed to warm to room temperature over 1.5 hours, then cooled to 0° C. and acidified with aqueous hydrochloric acid (10%). The layers were separated and the aqueous phase was washed with ethyl acetate. The aqueous layer was then made basic with aqueous sodium hydroxide (10N) and extracted with ethyl acetate (3×50 mL). The combined organic phase was dried over anhydrous sodium sulfate and filtered. Evaporation of solvents gave (S)-2-(1-azabicyclo[2.2.2]oct-3-yl)-5-methoxy-1(2H)-isoquinolinone as a white solid (0.23 g, 0.804 mmol). Preparation of the hydrochloride salt from ethanol-hydrogen chloride gave (S)-2-(1-azabicyclo[2.2.2]oct-3-yl)-5-methoxyl-1(2H)-isoquinolinone hydrochloride, m.p. 275°–277° C., $[\alpha]_D^{25}$ –106.7° (c=0.30, H$_2$O).

Proceeding as in Example 2, but replacing (S)-N-(1-azabicyclo[2.2.2]oct-3-yl)-3-methoxy-2-methylbenzamide with (S)-N-(1-azabicyclo[2.2.2]oct-3-yl)-2,3-dimethylbenzamide, from Example 1, Method A, gave (S)-2-(1-azabicyclo[2.2.2]oct-3-yl)-5-methyl-1(2H)-isoquinolinone hydrochloride, m.p. 265°–266° C., $[\alpha]_D^{25}$ –23.3° (c=0.52 H$_2$O).

Proceeding as in Example 2, but replacing (S)-N-(1-azabicyclo[2.2.2]oct-3-yl)-3-methoxy-2-methylbenzamide with (S)-N-(1-azabicyclo[2.2.2]oct-3-yl)-3-ethyl-2-methylbenzamide, from Example 1, Method B, gave (S)-2-(1-azabicyclo[2.2.2]oct-3-yl)-5-ethyl-1 (2H)-isoquinoline hydrochloride, m.p. >290° C., $[\alpha]_D^{25}$ –38.9° (c=0.18, H$_2$O).

Proceeding as in Example 2, but replacing (S)-N-(1-azabicyclo[2.2.2]oct-3-yl)-3-methoxy-2-methylbenzamide with endo-N-(8-methyl-8-azabicyclo[3.2.1]oct-3-yl)-3-methoxy-2-methylbenzamide, from Example 1, Method B, gave endo-2-(8-methyl-8-aza-bicyclo[3.2.1]oct-3-yl)-5-methoxy-1(2H)-isoquinolinone, m.p. 273°–275° C.

Proceeding as in Example 2, but replacing (S)-N-(1-azabicyclo[2.2.2]oct-3-yl)-3-methoxy-2-methylbenzamide with (S)-N-(1-azabicyclo[2.2.2]oct-3-yl)-3-chloro-2-methylbenzamide, from Example 1, Method A, gave (S)-2-(1-azabicyclo[2.2.2]oct-3-yl)-5-chloro-1(2H)-isoquinolinone hydrochloride, m.p. 287°–288° C., $[\alpha]_D^{25}$ –22.4° (c=0.03, H$_2$O).

Proceeding as in Example 2, but replacing (S)-N-(1-azabicyclo[2.2.2]oct-3-yl)-3-methoxy-2-methylbenzamide with (RS)-N-(1-azabicyclo[2.2.2]oct-3-yl)-2-ethyl-3-methylbenzamide, from Example 1, Method B, gave (RS)-2-(1-azabicyclo[2.2.2]oct-3-yl)4,5-dimethyl-1 (2H)-isoquinolinone hydrochloride, m.p. 275° C.

Proceeding as in Example 2, but replacing (S)-N-(1-azabicyclo[2.2.2]oct-3-yl)-3-methoxy-2-methylbenzamide with (RS)-N-(1-azabicyclo[2.2.2]oct-3-yl)-2-methylbenzamide, from Example 1, Method A, gave (RS)-2-(1-azabicyclo[2.2.2]oct-3-yl)-1(2H)-isoquinolinone hydrochloride, m.p. 130°–131° C.

Proceeding as i n Example 2, but replacing (S)-N-(1-azabicyclo[2.2.2]oct-3-yl)-3-methoxy-2-methylbenzamide with (RS)- N-(1-azabicyclo[2.2.2]oct-3-yl)-2-benzylbenzamide, from Example 1, Method A, gave (RS)-2-(1-azabicyclo[2.2.2]oct-3-yl)-4-phenyl-1(2H)-isoquinolinone hydrochloride, m.p. 207°–208° C.

Proceeding as in Example 2, but replacing (S)-N-(1-azabicyclo[2.2.2]oct-3-yl)-3-methoxy-2-methylbenzamide with (S)-N-(1-azabicyclo[2.2.2]oct-3-yl)-2-benzylbenzamide, from Example 1, Method A, gave (S)-2-(1-azabicyclo[2.2.2]oct-3-yl)-4-phenyl-1(2H)-isoquinolinone hydrochloride, m.p. 241°–242° C., $[\alpha]_D^{25}$ –12.0° (c=0.80 H$_2$O).

Proceeding as in Example 2, but replacing (S)-N-(1-azabicyclo[2.2.2]oct-3-yl)-3-methoxy-2-methylbenzamide with (S)-N-(1-azabicyclo[2.2.2]oct-3-yl)-2-butylbenzamide, from Example 1, Method A, gave (S)-2-(1-azabicyclo[2.2.2]oct-3-yl)-4-propyl-1(2H)-isoquinolinone hydrochloride, m.p. 155° C., $[\alpha]_D^{25}$ −37.3° (c=0.90, H$_2$O).

Proceeding as in Example 2 the following are prepared:

2-(1-azabicyclo[2.2.2]oct-4-yl)-1(2H)-isoquinolinone;

endo-2-(9-methyl-9-azabicyclo[3.3.1]non-3-yl)-1(2H)-isoquinolinone;

exo-2-(9-methyl-9-azabicyclo[3.3.1]non-3-yl)-1(2H)-isoquinolinone;

endo-2-(8-methyl-8-azabicyclo[3.2.1]oct-3-yl)-1(2H)-isoquinolinone;

exo-2-(8-methyl-8-azabicyclo[3.2.1]oct-3-yl)-1(2H)-isoquinolinone;

endo-2-(1-azabicyclo[3.3.1]non-4-yl)-1(2H)-isoquinolinone; and exo-2-(1-azabicyclo[3.3.1]non-4-yl)-1(2H)-isoquinolinone; and their pharmaceutically acceptable salts.

EXAMPLE 3

(S)-2-(1-azabicyclo[2.2.2]oct-3-yl)-5-ethyl-3,4-dihydro-1(2H)-isoquinolinone

The following is the preparation of a compound of Formula I via Scheme I, Step 3 in which the optional bond is absent;

X is ethyl in the 5-position;

Y is hydrogen;

R$^1$ is hydrogen; and

R$^2$ is (S)-1-azabicyclo[2.2.2]oct-3-yl.

(S)-2-(1-Azabicyclo[2.2.2]oct-3-yl)-5-ethyl-1(2H)-isoquinolinone (0.49 g, 1.5 mmol), from Example 2, was dissolved in methanol (10 ml) and reduced with hydrogen and 10% palladium on carbon at 50 psi for 5 hours. Filtration to remove the catalyst and evaporation of the methanol gave (S)-2-(1-azabicyclo[2.2.2]oct-3-yl)-5-ethyl-3,4-dihydro-1(2H)-isoquinolinone (0.48 g, 1.68 mmol), m.p. >290° C., $[\alpha]_D^{25}$ −40.3° (c=0.64 H$_2$O ).

Proceeding as in Example 3, but replacing (S)-2-(1-azabicyclo[2.2.2]oct-3-yl)-5-ethyl-1(2H)-isoquinolinone with (RS)-2-(1-azabicyclo[2.2.2]oct-3-yl )1(2H)-isoquinolinone, from Example 2, gave (RS)-2-(1-azabicyclo[2.2.2]oct-3-yl)-3,4-dihydro-1(2H)-isoquinolinone, m.p. 230°–232° C.

Proceeding as in Example 3, but replacing (S)-2-(1-azabicyclo[2.2.2]oct-3-yl)-5-ethyl-1(2H)-isoquinolinone with (RS)-2-(1-azabicyclo[2.2.2]oct-3-yl)-5-methyl-1(2H)-isoquinolinone, from Example 2, gave (RS)-2-(1-azabicyclo[2.2.2]oct-3-yl)-3,4-dihydro-5-methyl-1(2H)-isoquinolinone, m.p. >270° C.

Proceeding as in Example 3, but replacing (S)-2-(1-azabicyclo[2.2.2]oct-3-yl)-5-ethyl1(2H)-isoquinolinone with (S)-2-(1-azabicyclo[2.2.2]oct-3-yl )-5-methyl-1-(2H)-isoquinolinone, from Example 2, gave (S)-2-(1-azabicyclo[2.2.2]oct-3-yl )-3,4-dihydro-5-methyl-1(2H)-isoquinolinone, m.p. >300° C., $[\alpha]_D^{25}$ −44.2° (c=0.66, H$_2$O).

Proceeding as in Example 3, but replacing (S)-2-(1-azabicyclo[2.2.2]oct-3-yl)-5-ethyl-1(2H)-isoquinolinone with (S)-2-(1-azabicyclo[2.2.2]oct-3-yl)-5-methoxy-1(2H)-isoquinolinone, from Example 2, gave (S)-2-(1-azabicyclo [2.2.2]oct-3-yl)-3,4-dihydro-5-methoxy-1(2H)-isoquinolinone, m.p. >290° C. $[\alpha]_D^{25}$ −45.7° (c=0.16 H$_2$O).

EXAMPLE 4

(RS)-2-(1-azabicyclo[2.2.2]oct-3-yl)-4-bromo-1(2H)-isoquinolinone

The following is the preparation of a compound of Formula I in which the optional bond is present;

X and Y are hydrogen;

R$^1$ is bromo; and

R$^2$ is (S)-1-azabicyclo[2.2.2]oct-3-yl.

A solution of Br$_2$ (1.0M) in glacial acetic acid (0.8 mL) was added to a solution of (RS)-2-(1-azabicyclo[2.2.2]oct-3-yl)-1(2H)-isoquinolinone (0.20 g; 0.787 mmol), from Example 2, in glacial acetic acid (5.0 mL). The solvent was removed under pressure and the residue was partitioned between methylene chloride (100 ml) and sodium carbonate (2.0M, 30 ml). The organic phase was separated and dried over anhydrous sodium sulfate. The mixture was then filtered and concentrated under reduced pressure. The solid residue was dissolved in ethyl alcohol (2 ml) and the solution acidified with hydrochloric acid (10%). A small amount of ethyl ether was added and crystals were collected and dried in vacuo to give (RS)-2-(1-azabicyclo[2.2.2]oct-3-yl)-4-bromo-1(2H)-isoquinolinone (0.0832 g, 0.248 mmol), m.p. 208°–209° C.

EXAMPLE 5

The following are representative pharmaceutical formulations containing a compound of Formula I.

ORAL FORMULATION

A representative solution for oral administration contains:

| Compound of Formula I | 100–1000 mg |
|---|---|
| Citric Acid Mono hydrate | 105 mg |
| Sodium Hydroxide | 18 mg |
| Flavouring | q.s. |
| Water | to 100 ml |

INTRAVENOUS FORMULATION

A representative solution for intravenous administration contains:

| Compound of Formula I | 10–100 mg |
|---|---|
| Dextrose Monohydrate | q.s to make isotonic |
| Citric Acid Monohydrate | 1.05 mg |
| Sodium Hydroxide | 0.18 mg |
| Water for Injection | to 1.0 ml |

TABLET FORMULATION

A representative tablet form of a compound of Formula I may contain:

| Compound of Formula I | 1% |
| --- | --- |
| Microcrystalline cellulose | 73% |
| Stearic Acid | 25% |
| Colloidal Silica | 1% |

EXAMPLE 6

5-HT$_3$ RECEPTOR BINDING ASSAY

The following describes an in vitro assay for determining the 5-HT$_3$ receptor binding affinity of compounds of Formula I. The method is essentially that described by Kilpatrick et al., previously cited, which measures the affinity for 5-HT$_3$ receptors of the rat cerebral cortex radiolabelled with [$^3$H]quipazine.

Membranes are prepared from the cerebral cortices of rat brains homogenized in 50 mM Tris buffer (pH 7.4 at 4° C.) using a Polytron P10 tissue disrupter (setting 10, 2×10 sec bursts). The homogenate is centrifuged at 48,000×g for 12 min and the pellet obtained is washed, by resuspension and centrifugation, three times in homogenizing buffer. The tissue pellets are resuspended in the assay buffer, and are stored under liquid nitrogen until required.

The binding assays are conducted using a Tris-Krebs assay buffer of the following composition (mM): NaCl, 154; KCl, 5.4; KH$_2$PO$_4$, 1.2; CaCl$_2$.2H$_2$O, 2.5; MgCl$_2$, 1.0; glucose, 11; Tris, 10. Assays are conducted at 25° C. at 7.4 in a final volume of 0.25 ml. Zacopride (1.0 µM) is used to define the non-specific binding (NSB). 5-HT$_3$ receptors present in rat cortical membranes are labelled using 0.3–0.7 nM [$^3$H]quipazine (specific activity 50–66 Ci/mmol; New England Nuclear) in the presence of 0.1 µM paroxetine to prevent [$^3$H]quipazine binding to 5-HT uptake sites. The rat cortex membranes are incubated with [$^3$H]quipazine in the presence of 10 different concentrations of test compound ranging from 1×10$^{-12}$ to 1×10$^{-4}$ molar. Incubations are conducted for 45 min at 25° C. and are terminated by vacuum filtration over Whatman GF/B glass fiber filters using a Brandel 48 well cell harvester. After filtration the filters are washed for 8 sec with 0.1M NaCl. The filters are pretreated with 0.3% polyethyleneimine 18 hr prior to use in order to reduce filter binding of the radioligand. Radioactivity retained on the filters is determined by liquid scintillation counting.

The concentration of test compound producing 50% inhibition of radioligand binding is determined by an iterative curve fitting procedure. Affinities are expressed as the negative logarithm of the IC$_{50}$ value (pIC$_{50}$). Compounds of Formula I exhibit 5-HT$_3$ receptor binding affinity, i.e., pIC$_{50}$ values greater than 6.

EXAMPLE 7

5-HT$_3$ RECEPTOR ANTAGONIST ASSAY (VON BEZOLD-JARISCH REFLEX)

The following describes an in vivo method for determining the 5-HT$_3$ antagonist activity of compounds of Formula I. The method is a modified version of that described by Butler et al., Cohen et al., and Fozard, all previously cited, in which the 5-HT$_3$ selective agonist 2-methyl-5-hydroxytryptamine (2-m-5-HT) is substituted for 5-HT.

Male Sprague-Dawley rats, 250–380 grams, are anesthetized with urethane (1.4 g/kg, i.p.). A tracheotomy is performed and a tube is inserted into the trachea to facilitate respiration. Jugular and femoral veins are canulated for intravenous administration of drug. The duodenum is canulated for intraduodenal administration of drug. Heart rate is monitored by Gould ECG/Biotech amplifiers. After at least a 30 min equilibration period and prior to administration of test compound, control responses to intravenous administration of 2-m-5-HT are determined and a minimal dose producing sufficient and consistent bradycardia is chosen.

Potency

Intravenous challenges to 2-m-5-HT are administered every 12 minutes. Either vehicle or test compound is administered intravenously 5 minutes before each challenge to 2-m-5-HT. Each successive administration of test compound is increased in dosage until responses to 2-m-5-HT are blocked.

Duration

Vehicle or test compound is administered intravenously or intraduodenally and subsequent challenges to 2-m-5-HT are administered at 5, 15, 30, 60, 120, 180, 240, 300 and, in some instances, 360, 420 and 480 minutes post dose.

For both potency and duration studies heart rate (beats/min) is recorded continuously for the duration of the study. Responses to 2-m-5-HT are represented by the peak decrease in heart rate. Effects of test compounds are represented as percent inhibition of the bradycardia induced by 2-m-5-HT. Data are analyzed by a one-way repeated measures ANOVA and followed by pairwise comparison to vehicle control using Fisher's LSD strategy. From a dose-response curve so constructed, an ID$_{50}$ value is obtained to represent the dose that inhibited 50% of the bradycardia induced by 2-m-5HT.

EXAMPLE 8

FERRET, ANTI-EMESIS ASSAY

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cisplatin is injected i.v. at 10 mg/kg. The animals are then observed continuously for a 5 hour period and emetic responses (i.e., vomiting and/or retching) are recorded. For purposes of this example and that of Example 11, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Proceeding as in Example 8 but administering the test compounds by oral route, the anti-emetic effects of compounds of Formula I may be evaluated.

EXAMPLE 9

DOG, ANTI-EMESIS ASSAY

The following describes the procedure for determining the intravenous (i.v.) effects of compounds of Formula I on cisplatin-induced emesis in dogs.

Male and female dogs (6–15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

EXAMPLE 10

PROKINETIC ASSAY

The following describes an in vivo method of determining the prokinetic activity of the compounds of Formula I by measuring the rate of gastric emptying of test meal in rats. The method is that described by Droppleman et al., previously cited.

Test meal is prepared by slowly adding 20 grams of cellulose gum (Hercules Inc., Wilmington, Del.) to 200 ml of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 ml of warm water and then blended into the cellulose solution followed by 16 g of purified casein (Sigma Chemical Co., St. Louis, Mo.), 8 g of powdered confectioners sugar, 8 g of cornstarch, and 1 g of powdered charcoal. Each ingredient is added slowly and mixed thoroughly resulting in approximately 325 ml of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 ml of test meal is orally administered to each rat with a 5.0 ml disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 ml weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955, 1096–112).

EXAMPLE 11

ANXIOLYTIC BEHAVIOR ASSAY

The following describes an in vivo method for determining anxiolytic activity of compounds of Formula I.

Naive male C5Bl/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is relected by increased latency (the time for the mouse to move to the dark chamber when first placed in the center of the lighted area), increase in shuttle activity, increased or unaltered locomotor activity (number of grid lines crossed) and decreased time spent in the dark compartment.

EXAMPLE 12

WITHDRAWAL ANXIETY ASSAY

The following procedure describes a method to determine whether compounds of Formula I effect the anxiety that occurs after abruptly ceasing chronic treatment with drugs of abuse.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 11). Anxiolysis is seen as a general increase in exploratory activity in the lighted area. An increase in exploratory activity is relected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0% w/v in drinking water), nicotine (0.1 mg/kg, i.p., twice daily) or cocaine (1.0 mg/kg, j.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawl phase by intraperitoneal injection. Responses are represented as inhibition of the decrease in anxiolytic behavior after the ethanol, cocaine or nicotine treatment is ceased.

EXAMPLE 13

COGNITIVE ENHANCEMENT ASSAY

The following describes a model to determine the cognitive enhancing effects of compounds of Formula I.

Young adult and aged BKW mice are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 11). Mice are exposed to the two-compartment test area over a 3 day period. The young mice habituate to the test area by day 3 and spend less time exploring the lighted area, whereas exploratory activity in the lighted area remains constant through day 3 for the aged mice. Exploratory activity is seen as latency (the time for the mouse to move to the dark chamber when first placed in the center of the lighted area), locomotor activity (number of grid lines crossed), number of rears and time spent in the lighted compartment. Vehicle or test compounds are administered to the aged mice by intraperitoneal injection. Cognitive enhancing effects in the aged rats are reflected by a decrease in exploratory activity by day 3.

We claim:

1. A compound of Formula I:

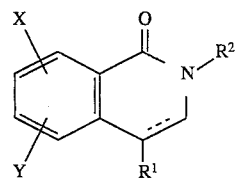

in which:

X and Y are independently hydrogen, halogen, hydroxy, lower alkoxy, lower alkyl, nitro, amino, aminocarbonyl, (lower alkyl)amino, di(lower alkyl)amino, or (lower alkanoyl)amino;

$R^1$ is hydrogen, lower alkyl, phenyl or halogen;

$R^2$ is a group of Formulae (a), (b), (c), or (d):

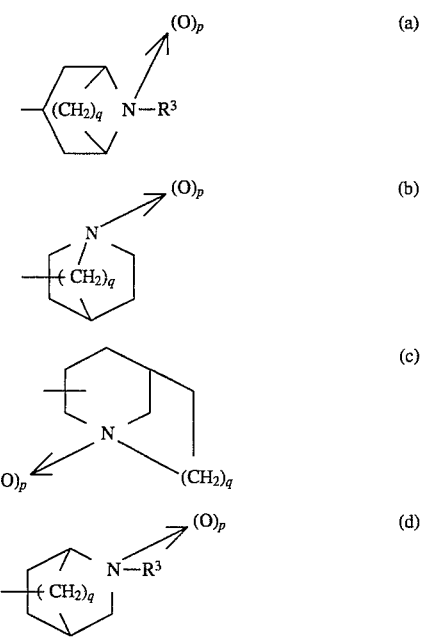

in which:

p is 0 or 1;

q is 1, 2 or 3; and $R^3$ is $C_{1-7}$ alkyl, $C_{3-8}$ cycloalkyl, $C_{3-8}$ cycloalkyl-$C_{1-2}$ alkyl, or a group $(CH_2)_t R^4$ where t is 1 or 2 and $R^4$ is thienyl, pyrrolyl, or furyl, each optionally further substituted by one or two substituents being $C_{1-6}$ alkyl, $C_{1-6}$ alkoxy, trifluoromethyl or halogen, or is phenyl optionally substituted by one or two substituents being $C_{1-4}$ alkoxy, trifluoromethyl, halogen, nitro, carboxy, esterified carboxy, or $C_{1-4}$ alkyl optionally substituted by hydroxy, $C_{1-4}$ alkoxy, carboxy, esterified carboxy or in vivo hydrolyzable acyloxy; and the dashed line denotes an optional bond, except that the bond is present when $R^1$ is halogen or $R^2$ is a group of Formula (a); or a pharmaceutically acceptable salt, or an individual isomer or mixtures of isomers thereof.

2. A compound of claim 1 in which p is 0, X and Y are independently hydrogen, halogen, lower alkyl, or lower alkoxy; and $R^2$ is 1-azabicyclo[2.2.2]oct-3-yl;

1-azabicyclo[2.2.2]oct-4-yl;

endo-9-methyl-9-azabicyclo[3.3.1]non-3-yl;

exo-9-methyl-9-azabicyclo[3.3.1]non-3-yl;

endo-8-methyl-8-azabicyclo[3.2.1]oct-3-yl;

exo-8-methyl-8-azabicyclo[3.2.1]oct-3-yl;

endo-1-azabicyclo[3.3.1]non-4-yl; or exo-1-azabicyclo[3.3.1]non-4-yl.

3. A compound of claim 2 in which Y is hydrogen and $R^2$ is 1-azabicyclo[2.2.2]oct-3-yl.

4. A compound of claim 3 in which X is lower alkyl or lower alkoxy and $R^1$ is hydrogen.

5. A compound of claim 4 in which the optional bond is present and X is methyl in the 5-position, namely 2-(1-azabicyclo[2.2.2]oct-3-yl)-5-methyl-1(2H)-isoquinolinone or a pharmaceutically acceptable salt thereof.

6. A compound of claim 5 which is (S)-2-(1-azabicyclo[2.2.2]oct-3-yl)-5-methyl-1(2H)-isoquinolinone or a pharmaceutically acceptable salt thereof.

7. A compound of claim 6 which is (S)-2-(1-azabicyclo[2.2.2]oct-3-yl)-5-methyl-1(2H)-isoquinolinone hydrochloride.

8. A compound of claim 5 which is (R)-2-(1-azabicyclo[2.2.2]oct-3-yl)-5-methyl-1(2H)-isoquinolinone or a pharmaceutically acceptable salt thereof.

9. A compound of claim 8 which is (R)-2-(1-azabicyclo[2.2.2]oct-3-yl)-5-methyl-1(2H)-isoquinolinone hydrochloride.

10. A compound of claim 4 wherein the optional bond is present and X is ethyl in the 5-position, namely 2-(1-azabicyclo[2.2.2]oct-3-yl)-5-ethyl-1(2H)-isoquinolinone or a pharmaceutically acceptable salt thereof.

11. A compound of claim 10 which is (S)-2-(1-azabicyclo[2.2.2]oct-3-yl)-5-ethyl-1(2H)-isoquinolinone or a pharmaceutically acceptable salt thereof.

12. A compound of claim 11 which is (S)-2-(1-azabicyclo[2.2.2]oct-3-yl)-5-ethyl-1(2H)-isoquinolinone hydrochloride.

13. A compound of claim 10 which is (R)-2-(1-azabicyclo[2.2.2]oct-3-yl)-5-ethyl-1(2H)-isoquinolinone or a pharmaceutically acceptable salt thereof.

14. A compound of claim 13 which is (R)-2-(1-azabicyclo[2.2.2]oct-3-yl)-5-ethyl-1(2H)-isoquinolinone hydrochloride.

15. A compound of claim 4 wherein the optional bond is present and X is methoxy in the 5-position, namely 2-(1-azabicyclo[2.2.2]oct-3-yl)-5-methoxy-1(2H)-isoquinolinone or a pharmaceutically acceptable salt thereof.

16. A compound of claim 15 which is (S)-2-(1-azabicyclo[2.2.2]oct-3-yl)-5-methoxy-1(2H)-isoquinolinone or a pharmaceutically acceptable salt thereof.

17. A compound of claim 16 which is (S)-2-(1-azabicyclo[2.2.2]oct-3-yl)-5-methoxy-1(2H)-isoquinolinone hydrochloride.

18. A compound of claim 15 which is (R)-2-(1-azabicyclo[2.2.2]oct-3-yl)-5-methoxy-1(2H)-isoquinolinone or a pharmaceutically acceptable salt thereof.

19. A compound of claim 18 which is (R)-2-(1-azabicyclo[2.2.2]oct-3-yl)-5-methoxy-1(2H)-isoquinolinone hydrochloride.

20. A compound of claim 4 wherein the optional bond is absent and X is methyl in the 5-position, namely 2-(1-azabicyclo[2.2.2]oct-3-yl)-3,4-dihydro-5-methyl-1(2H)-isoquinolinone or a pharmaceutically acceptable salt thereof.

21. A compound of claim 20 which is (S)-2-(1-azabicyclo[2.2.2]oct-3-yl)-3,4-dihydro-5-methyl-1(2H)-isoquinolinone or a pharmaceutically acceptable salt thereof.

22. A compound of claim 21 which is (S)-2-(1-azabicyclo[2.2.2]oct-3-yl)-3,4-dihydro-5-methyl-1(2H)-isoquinolinone hydrochloride.

23. A compound of claim 20 which is (R)-2-(1-azabicyclo[2.2.2]oct-3-yl)-3,4-dihydro-5-methyl-1(2H)-isoquinolinone or a pharmaceutically acceptable salt thereof.

24. A compound of claim 23 which is (R)-2-(1-azabicyclo[2.2.2]oct-3-yl)-3,4-dihydro-5-methyl-1(2H)-isoquinolinone hydrochloride.

25. A compound of claim 4 wherein the optional bond is absent and X is ethyl in the 5-position, namely 2-(1-azabicyclo[2.2.2]oct-3-yl)-3,4-dihydro-5-ethyl-1(2H)-isoquinolinone or a pharmaceutically acceptable salt thereof.

26. A compound of claim 25 which is (S)-2-(1-azabicyclo[2.2.2]oct-3-yl)-3,4-dihydro-5-ethyl-1(2H)-isoquinolinone or a pharmaceutically acceptable salt thereof.

27. A compound of claim 26 which is (S)-2-(1-azabicyclo[2.2.2]oct-3-yl)-3,4-dihydro-5-ethyl-1(2H)-isoquinolinone hydrochloride.

28. A compound of claim 25 which is (R)-2-(1-azabicyclo[2.2.2]oct-3-yl)-3,4-dihydro-5-ethyl-1(2H)-isoquinolinone or a pharmaceutically acceptable salt thereof.

29. A compound of claim 28 which is (R)-2-(1-azabicyclo[2.2.2]oct-3-yl)-3,4-dihydro-5-ethyl-1(2H)-isoquinolinone hydrochloride.

30. A compound of claim 4 wherein the optional bond is absent and X is methoxy in the 5-position, namely 2-(1-azabicyclo[2.2.2]oct-3-yl)-3,4-dihydro-5-methoxy-1(2H)-isoquinolinone or a pharmaceutically acceptable salt thereof.

31. A compound of claim 30 which is (S)-2-(1-azabicyclo[2.2.2]oct-3-yl)-3,4-dihydro-5-methoxy-1(2H)-isoquinolinone or a pharmaceutically acceptable salt thereof.

32. A compound of claim 31 which is (S)-2-(1-azabicyclo[2.2.2]oct-3-yl)-3,4-dihydro-5-methoxy-1(2H)-isoquinolinone hydrochloride.

33. A compound of claim 30 which is (R)-2-(1-azabicyclo[2.2.2]oct-3-yl)-3,4-dihydro-5-methoxy-1(2H)-isoquinolinone or a pharmaceutically acceptable salt thereof.

34. A compound of claim 33 which is (R)-2-(1-azabicyclo[2.2.2]oct-3-yl)-3,4-dihydro-5-methoxy-1(2H)-isoquinolinone hydrochloride.

35. A pharmaceutical composition comprising a therapeutically effective amount of a compound of claim 1 in combination with a pharmaceutically acceptable excipient.

36. A method for treating a disease which is emesis, a gastrointestinal disorder, a CNS disorder, a cardiovascular disorder or pain in an animal in need thereof, which method comprises administering a therapeutically effective amount of a compound of claim 1 to such animal.

37. The method of claim 36 wherein the disease is emesis.

38. The method of claim 36 wherein the disease is a gastrointestinal disorder.

39. The method of claim 36 wherein the disease is a CNS disorder.

40. The method of claim 36 wherein the disease is a cardiovascular disorder.

41. The method of claim 36 wherein the disease is pain.

\* \* \* \* \*